United States Patent
Marshall et al.

[11] Patent Number: 5,913,868
[45] Date of Patent: Jun. 22, 1999

[54] BLOOD SAMPLING DEVICES

[75] Inventors: Jeremy Marshall; David Danvers Crossman, both of Oxford, United Kingdom

[73] Assignee: Owen Mumford Limited, Oxford, United Kingdom

[21] Appl. No.: 08/782,153

[22] Filed: Jan. 13, 1997

Related U.S. Application Data

[63] Continuation-in-part of application No. PCT/GB95/01652, Jul. 12, 1995.

[30] Foreign Application Priority Data

Jul. 13, 1994 [GB] United Kingdom .................. 9414143
Feb. 17, 1996 [GB] United Kingdom .................. 9603311

[51] Int. Cl.[6] .................................................. A61B 17/34
[52] U.S. Cl. ............................................................ 606/181
[58] Field of Search ................................. 606/181, 182, 606/184, 185

[56] References Cited

U.S. PATENT DOCUMENTS 4,889,117  12/1989  Stevens .................................. 606/181
5,324,302   6/1994  Crouse .................................... 606/181
5,385,571   1/1995  Morita .................................... 606/181

FOREIGN PATENT DOCUMENTS 2 595 237   9/1987   France .

*Primary Examiner*—Michael Buiz
*Assistant Examiner*—Kevin Truong
*Attorney, Agent, or Firm*—Young & Thompson

[57] ABSTRACT

A lancet has a needle (2) embedded in a plastics body (1), its tip (3) projecting from the forward end but being initially encased in a cap (4). This cap (4) may be integrally moulded with the body, around the needle tip (3), and be sheared away before use. The needle (2) can be pushed back in relation to the body (1) after use, conveniently by applying the cap (4) to the tip (3), until the tip is safely flush with, or set back with respect to the leading end of the body (1). The rear end of the body (1) has a structure (9) to prevent the rear end of the needle (2) being pushed forwards again. To ensure that the tip disappears, the body (1) may be formed with an intermediate, resiliently flexible bridge (19) stiff enough to remain rigid during pricking. But when the needle (2) is forced back and pressure is also applied to the part of the body forward of the bridge (19), the needle (2) and that forward part move back with respect to the rear part of the body. Then the forward part is released to move forwards, sprung by the bridge (19), leaving the needle held by the rear part.

13 Claims, 4 Drawing Sheets

BLOOD SAMPLING DEVICES

This is a continuation-in-part application of International Application PCT/GB95/01562 filed Jul. 12, 1995, which designated the United States.

This invention relates to blood sampling devices, and in particular to a lancet for pricking the skin to draw a small drop of blood for analysis. Such prickers are widely used by diabetics, for example, who need to know their sugar level, However, there are many other applications.

There is an obvious need to make the sharp tip of the lancet safe after use. There have been various proposals for having the lancet as part of a cheap, disposable device which, after a single use, can be thrown away with the lancet automatically retracted inside the body and thus made safe. These are very handy, but in the long run it is more expensive to use them than to have a permanent firing mechanism and to load it when required with a lancet. But then the lancet must be made safe after removal.

The usual form of lancet has a steel needle encased in an elongate plastics body. A cap is moulded integrally with this body and initially the tip of the needle is embedded in it. But the connection between the cap and the body is weak and the cap can be pulled free to expose the tip. After use, the cap may be used to cover the needle tip again, and it may be re-oriented to fit over the forward end of the body.

The needle tends to be smooth and the plastics material of the body does not have much grip on it. It can happen that, when breaking the cap free, the cap is squeezed or angled with respect to the body sufficiently to pull the needle forwardly by its tip with respect to the body. There is then a lancet with a needle tip extending too far.

There is also a trend towards making the needle thinner, to achieve an even sharper point, and therefore a less noticeable prick. But the needle also serves to give some strength to the lancet as a whole, providing a reinforcing rod along its axis. If it is too thin, the lancet is able to bend rather easily, and this is unsatisfactory.

It is the aim of aspects of this invention to remedy these faults.

According to the present invention there is provided a lancet for a skin pricker comprising a needle with a tip and an elongate body of moulded plastics material encasing most of the needle, which is movable rearwardly with respect to the body to retract the needle tip within the body after use, characterised in that the needle tip is initially encased by a breakaway cap integrally moulded with the body at its forward end and which is exposed when the cap is removed, in that the mutual engagement of the needle and body is such that the needle cannot move forwards from its initial position relative to the body and in that the needle and body remain effectively integral and move together during the act of skin pricking.

Instead of trying to place the cap back over the end of the lancet after use, the needle is pushed backwards in relation to the body until the tip is flush with or recessed into the forward end. However, there is still uncertainty that the tip will always be retracted sufficiently, but a modification should solve that problem.

Conveniently, the plastics body has a forward and a rearward part joined by a bridge which acts as a spring normally holding the parts distanced but which is compressible to allow the parts to approach, the hold on the needle of the rearward part being greater than that of the forward part. Thus when the needle is pushed rearwardly with a pusher also acting on the forward part, the latter closes up towards the rearward part and the needle is retracted, and when the pusher is removed the rearward part holds the needle while the forward part is sprung forward by the bridge to shield the needle tip.

Conveniently, the bridge is provided by an aperture diametrally through the body, and this aperture may be an enlargement of one of the apertures which are formed by elements which hold the needle while the body is moulded around it.

The aperture is preferably generally elliptical or lozenge shaped in cross section, the major axis of that section being transverse to the length of the body whereby in the normal, relaxed position, the ellipse or lozenge has a significant minor axis, but when the parts are pressed together this axis is reduced while the major axis slightly lengthens.

This difference in hold may simply be achieved by different frictional grips, the rearward part being substantially longer than the forward part and thus having a much greater surface area in contact with the needle.

Alternatively there could be a membrane at the rear end of the body against which the rear end of the needle bears during skin pricking, but which can be broken when the needle is urged rearwardly by a substantial force. Another possibility is a throat at the rear end of the body in which the rear end of the needle is trapped during skin pricking, but through which that rear end of the needle can be urged by a substantial force.

Conveniently, the cap is adapted to serve as an implement for pushing the tip of the needle, after use, back into the body. The forward end of the body may be recessed and the cap have a projection which can enter the recess when pushing the tip of the needle, thus helping to ensure that the needle tip is not left proud of the mouth of the recess. The rear end of the body will generally be adapted to shield the rear end of the needle when the needle is retracted, so that it cannot be accidentally pushed forwards again.

The impediment to forward movement of the needle from its initial position relative to the body may be achieved by a forwardly facing shoulder where the needle reduces in cross section to a leading length portion projecting from the body and terminating in the tip.

In that case the needle is generally cylindrical with a flat formed over the leading length portion to make the reduced cross section.

For a better understanding of the invention, some embodiments will now be described, by way of example, with reference to the accompanying drawings, in which.

Figure 1:
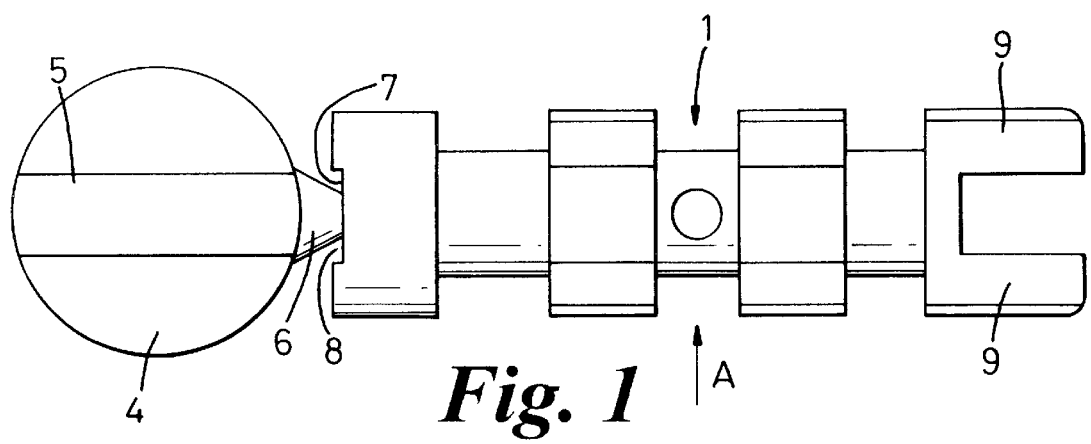
FIG. 1 is a side view of a lancet in a pre-use condition.

The lancet of FIGS. 1 to 5 has an elongate body 1 of moulded plastics material. It resembles the spool of a spool valve, having alternating large and small diameter sections. Co-axially encased within it there is a needle 2, indicated in broken lines in FIG. 2, which projects in a sharp tip 3 at the forward end.

This tip is initially encased in a cap 4 which is in the form of a disc with a diametral rib 5. This could be shortened to a central stud. The cap is integrally moulded with the body 1 and connects to it by a neck 6 which will be weak enough to be sheared off from end surface 7 by a twisting action. The forward end of the body 1 has a transverse recess 8 in which the surface 7 forms the base.

At the other end, the body 1 is extended by two opposed wings 9 projecting rearwardly. In the initial state, the rear end portion of the needle 2 is fully embedded in the body with its end face aligned with the roots of these wings.

Figure 3:
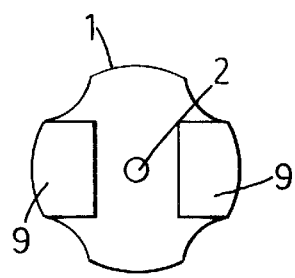
FIG. 3 is a rear end view of the lancet.

The larger diameter portions of the body 1, at least towards the rear, are not smoothly cylindrical on their outer surfaces. They have indentations as best seen in FIG. 3. This is to afford a grip for formations within the firing device to stop the body 1 rotating about its axis when the cap 4 is twisted off.

Figure 4:
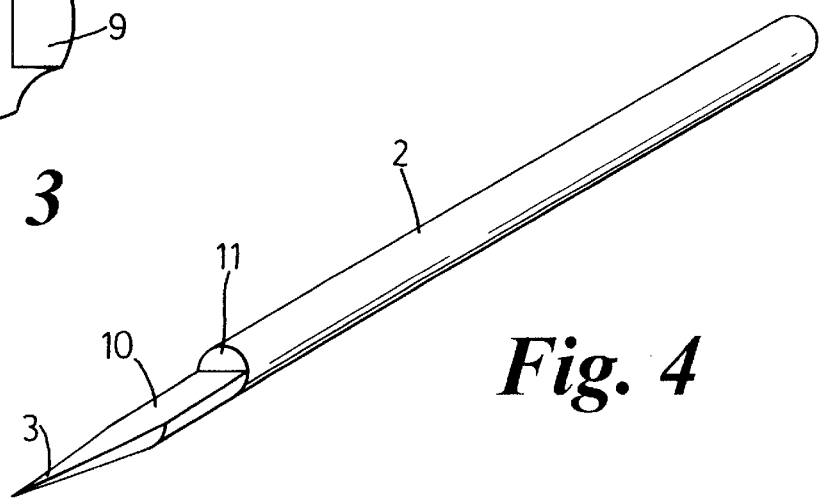
FIG. 4 is a perspective view of the needle that forms part of the lancet.
Figure 5A:
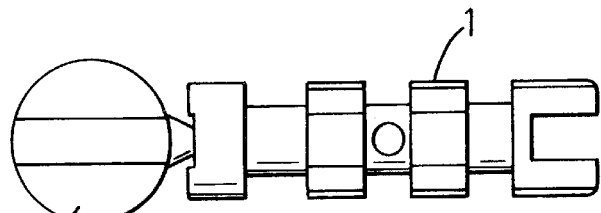
FIG. 5 shows stages of use of the lancet.
Figure 5B:
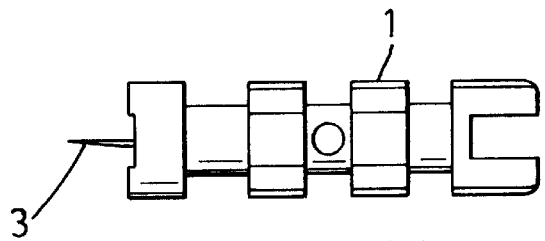
Figure 5C:
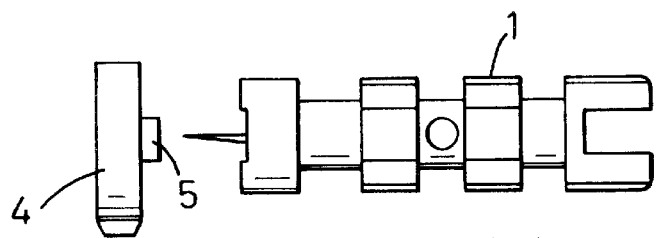
Figure 5D:
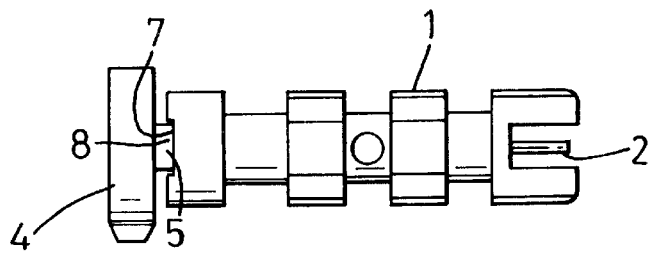
Figure 5E:
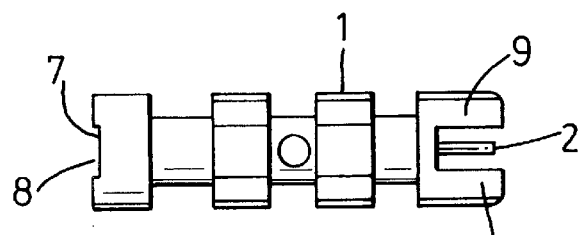

Referring to FIG. 4, the needle 2 is cylindrical over most of its length. But at its forward end a flat 10 is formed, conveniently by grinding, before or during the operation to produce the sharp tip 3. This flat extends back from the extremity of the tip to a radial, semi-circular shoulder 11.

Figure 2:
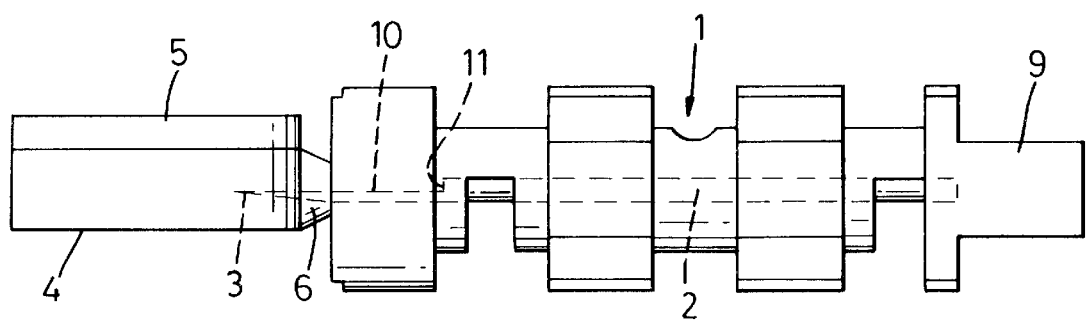
FIG. 2 is another side view of the lancet viewed in the direction A of FIG. 1, showing its encased needle.

Referring to FIG. 5, stage (a) shows the lancet in its pre-use state, as in FIGS. 1 and 2. The cap 4 is then twisted off to leave the needle tip 3 exposed as in stage (b). The pricker is then used. Although the needle 2 is slidable within the body 1 there is considerable friction preventing this. The resistance of the user's skin to the sharp tip will be substantially less than the force needed to shift the needle relative to the body, and so for the actual pricking operation the needle will remain fast with the body.

After use, the cap 4 is offered up as in stage (c) with its rib 5 towards the forward end of the lancet body. It is then pressed against it to achieve stage (d). Here, the rib 5 has pushed the needle rearwardly and entered the recess 8, so the tip of the needle is flush with the surface 7 and thus safe. At the same time, the rear end of the needle 2 projects, but is shielded between the wings 9. The cap can then be thrown away, and so can the lancet be discarded, it now being in the state illustrated at stage (e).

It will be appreciated that the shoulder 11 will stop the needle 2 being drawn forward out of the body 1 when the cap is removed, but will not impede the needle being pushed backwards.

Instead of relying on friction to hold the needle in the forward position during the pricking operation, other measures could be taken. For example, the body moulding could form a thin plastics membrane over the rear end of the needle. This would be strong enough to remain unbroken while the skin was being pricked, but weak enough to be pierced by the rear end of the needle when the cap was pushed against the tip. Another way would be to make a very small flat at the rear end of the needle, whose main length could be forced through the resultant slightly narrowed throat formed by the flat.

Referring to FIGS. 6 to 9, the construction of this lancet is largely similar to the one described and the same references indicate corresponding parts. Apart from the significant feature described below, the minor differences are that there is a domed stud 12 on the cap 4 rather than a rib 5, and that, instead of wings 9, there is a recess 13 at the rear of the body 1, initially empty but into which the rear end of the needle 2 projects when retracted.

Figure 6:
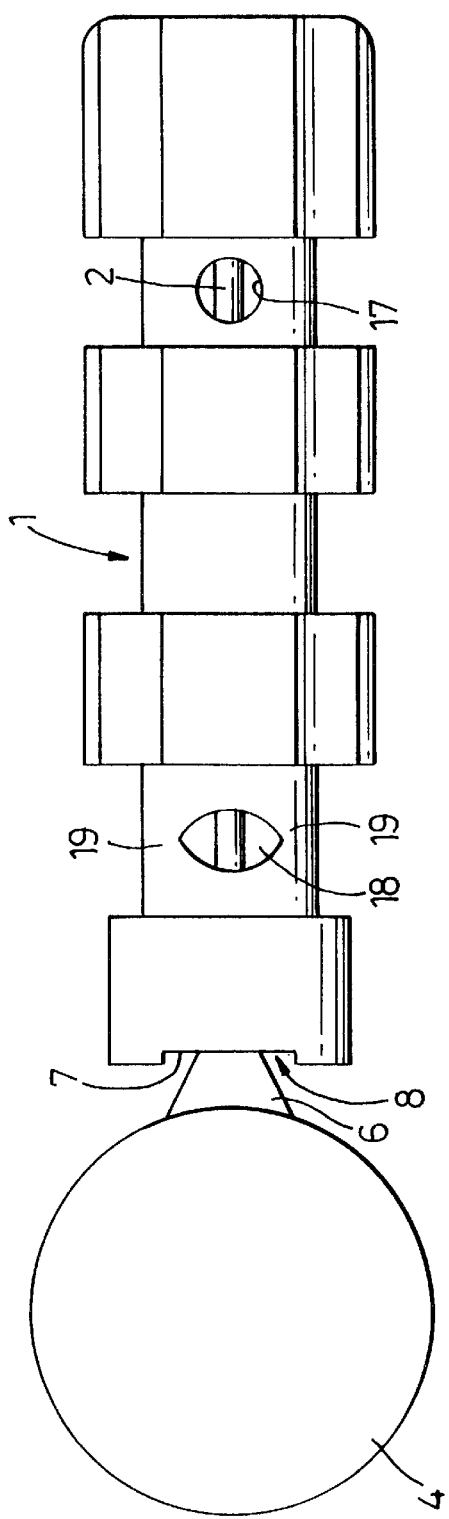
FIG. 6 is a side view of another lancet prior to use.

The significant difference lies in the leading small diameter portion 14 of the body 1. In the first embodiment this is recessed on one side as a result of the means which hold the needle while the body 1 is moulded. There is a similar recess at the rear end. But the body remains substantially rigid. In this second embodiment, there are still those recesses 15 and 16 and the rear one 15 opens into a small circular aperture 17 on the other side of the needle. This aperture may also be formed as a by-product of the moulding process, although it does not affect the local rigidity. But the forward recess 16 opens into an enlarged aperture 18 whose cross section is substantially elliptical or lozenge shaped with the major axis transverse to the length of the body 1. This creates a narrow bridge 19 at each side. In the normal, relaxed state as shown in FIG. 6, the minor axis of the ellipse or lozenge is about two thirds of the length of the major axis.

Figure 7:
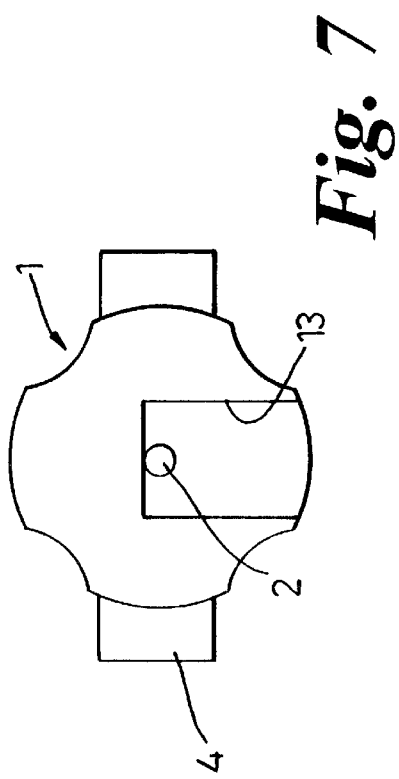
FIG. 7 is a rear end view of the lancet of FIG. 6.

For use, the cap 4 is twisted off, and the lancet is fired in the usual way. Afterwards, the cap 4 may be used to press the needle to a retracted position, using the stud 12 as shown in FIG. 7. As it is pressed against the needle tip 3, that will embed itself slightly, but the needle will be shifted rearwardly until the stud 5 meets the surface 7. Continued pressure, with the user holding the part of the body 1 to the rear of the portion 14, causes the aperture 18 to contract along its minor axis and expand slightly along its major axis as shown in FIG. 7. Meanwhile, the rear end of the needle projects into the recess 13.

Figure 8:
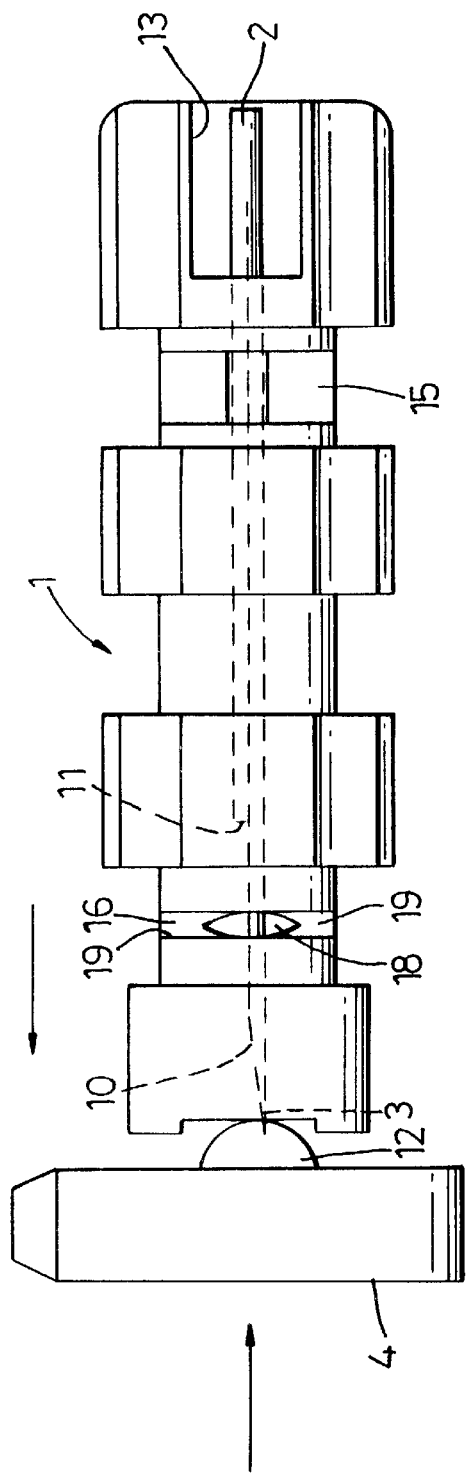
FIG. 8 is a side view of the lancet of FIG. 6 with the needle being retracted after use.
Figure 9:
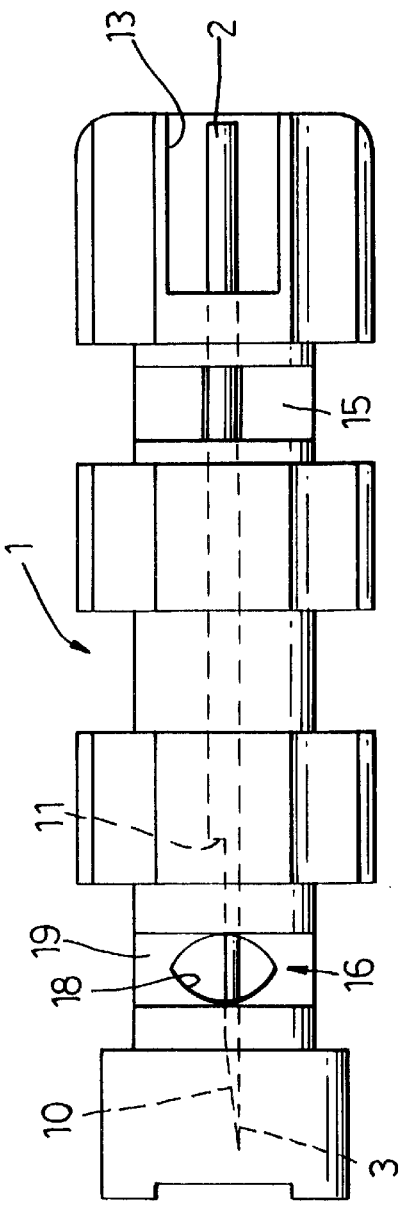
FIG. 9 is a side view of the lancet of FIG. 6 after retraction and ready to discard.

The cap 4 is then removed, and the bridges 18 being of resilient plastics material, act as springs pushing the forward part of the body 1 away from the rearward part so that the body 1 resumes its original configuration. But a much greater length of needle 2 is within the rearward part than the forward part, and the needle is therefore held by the frictional grip of the rearward part while the forward part slides forwards relative to the tip 3, which is left concealed as shown in FIG. 8. With the first embodiment, there is greater risk of the tip remaining exposed, particularly if it has embedded itself to some extent in the rib 5.

We claim:

1. A lancet for a skin pricker, the lancet comprising a needle with a tip and an elongate body with a forward end and rear end of moulded plastics material encasing most of the needle, the needle tip being initially encased by a breakaway cap integrally moulded with the body at its forward end and being exposed when the cap is removed, wherein the needle and body have co-operating formations that prevent the needle moving forwards from its initial position relative to the body, and wherein the needle is movable rearwardly with respect to the body to retract the needle tip within the body, the force required for this rearward movement being greater than the force required for the needle tip to penetrate skin.

2. A lancet as claimed in claim 1, wherein the plastics body has a forward part and a rearward part joined by a bridge which acts as a spring normally holding the parts distanced but which is compressible to allow the parts to approach, wherein the rearward part exerts a greater frictional grip on the needle than does the forward part, and wherein the expansion force of the compressed spring bridge is sufficient to overcome the frictional grip of the forward part whereby when the needle is pushed rearwardly with a pusher also acting on the forward part with a force sufficient to overcome the frictional grip of the rearward part, the forward part closes up towards the rearward part and the needle is retracted, and when the pusher is removed the rearward part holds the needle while the forward part is sprung forward relative to the needle by the bridge to shield the needle tip.

3. A lancet as claimed in claim 2, wherein the rearward part of the body is substantially longer than the forward part and thus has a much greater surface area in contact with the needle, thereby giving rise to the differential frictional grip of said parts on the needle.

4. A lancet as claimed in claim 2, wherein the bridge is provided by an aperture diametrally through the body.

5. A lancet as claimed in claim 4, wherein the diametral aperture is an enlargement of one of the apertures which are formed by elements which hold the needle while the body is moulded around it.

6. A lancet as claimed in claim 4, wherein the aperture is generally elliptical or lozenge shaped in cross section, the major axis of said section being transverse to the length of the body.

7. A lancet as claimed in claim 1, wherein a membrane is formed at the rear end of the body against which the rear end of the needle bears during skin pricking, but which can be broken when the needle is urged rearwardly by a substantial force.

8. A lancet as claimed in claim 1, wherein the hold on the needle of the rearward part is a throat is formed at the rear end of the body in which the rear end of the needle is trapped during skin pricking, but through which that rear end of the needle can be urged by a substantial force.

9. A lancet as claimed in claim 1, wherein the cap is adapated to serve as an implement for pushing the tip of the needle, after use, back into the body.

10. A lancet as claimed in claim 9, wherein the forward end of the body is recessed and the cap has a projection which can enter the recess when pushing the tip of the needle.

11. A lancet as claimed in claim 1, wherein the rear end of the body is adapted to shield the rear end of the needle when the needle is retracted.

12. A lancet as claimed in claim 1, wherein the needle formation is a forwardly facing shoulder where the needle reduces in cross section to a leading length portion projecting from the body and terminating in the tip.

13. A lancet as claimed in claim 12, wherein the needle is generally cylindrical with a flat formed over the leading length portion to make the reduced cross section.

* * * * *